United States Patent
Zagar et al.

(10) Patent No.: US 7,846,872 B2
(45) Date of Patent: Dec. 7, 2010

(54) HERBICIDAL MIXTURES CONTAINING PICOLINAFEN

(75) Inventors: Cyrill Zagar, Mannheim (DE); Adam F. Burnhams, Cary, NC (US); Peter Dombo, Wiesbaden (DE); Andreas Landes, Roemerberg-Heiligenstein (DE); Bernd Sievernich, Hassloch (DE); Herve R. Vantieghem, Stutensee-Staffort (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 555 days.

(21) Appl. No.: 10/548,841

(22) PCT Filed: Mar. 12, 2004

(86) PCT No.: PCT/EP2004/002633
§ 371 (c)(1),
(2), (4) Date: Sep. 13, 2005

(87) PCT Pub. No.: WO2004/081129
PCT Pub. Date: Sep. 23, 2004

(65) Prior Publication Data
US 2006/0211576 A1    Sep. 21, 2006

Related U.S. Application Data

(60) Provisional application No. 60/453,975, filed on Mar. 13, 2003.

(51) Int. Cl.
*A01N 43/90* (2006.01)
*A01N 37/10* (2006.01)
*A01N 43/42* (2006.01)

(52) U.S. Cl. ............... 504/118; 504/130; 504/144; 504/247

(58) Field of Classification Search ............ 504/116, 504/118, 130, 144, 247
See application file for complete search history.

(56) References Cited

U.S. PATENT DOCUMENTS

| | | | |
|---|---|---|---|
| 3,537,840 A | 11/1970 | Ames et al. | |
| 3,884,672 A | 5/1975 | Ahle | |
| 5,665,673 A | 9/1997 | Harr et al. | |
| 5,674,807 A | 10/1997 | Baltruschat | |
| 5,877,116 A | 3/1999 | Harr et al. | |
| 5,877,117 A | 3/1999 | Harr et al. | |
| 6,090,750 A * | 7/2000 | Chollet et al. | 504/105 |
| 6,849,578 B1 * | 2/2005 | Wellmann et al. | 504/130 |
| 2002/0039968 A1 * | 4/2002 | Aven et al. | 504/128 |

FOREIGN PATENT DOCUMENTS

| | | |
|---|---|---|
| CA | 1282974 | 7/1971 |
| CA | 1018789 | 10/1977 |
| CA | 1167270 | 5/1984 |
| CA | 2390564 A1 | 5/2002 |
| DE | 35 36 035 A | 4/1987 |
| EP | 0 208 245 A | 1/1987 |
| EP | 0 273 669 A | 7/1988 |
| EP | 0 347 950 A | 12/1989 |
| EP | 0 381 907 A | 8/1990 |
| FR | 2639-185 A | 5/1990 |
| WO | WO 94/07368 A | 4/1994 |
| WO | WO 00/78147 A | 12/2000 |
| WO | WO 01/26466 A | 4/2001 |
| WO | WO 01/74157 A | 10/2001 |
| WO | WO 02/15694 A | 2/2002 |

OTHER PUBLICATIONS

Tomlin et al., "The Pesticide Manual, Twelfth Edition" 2000, British Crop Protection Council, pp. 742-743.

* cited by examiner

*Primary Examiner*—Johann R Richter
*Assistant Examiner*—Andriae M Holt
(74) *Attorney, Agent, or Firm*—Rothwell, Figg, Ernst & Manbeck, P.C.

(57) ABSTRACT

A herbicidal mixture, comprising
A) picolinafen (I)

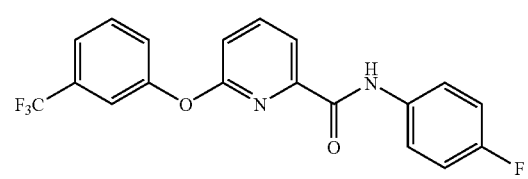

or an agriculturally useful salt thereof,
and
B) at least one further herbicide selected from the group of the phthalamates (B1), semicarbazones (B2), chloracetanilides (B3), carbamates (B4), pyridazines (B5), dinitrophenols (B6), dipyridylenes (B7), benzothiadiazoles (B8), uracils (B9), pyridazinones (B10), phenylcarbamates (B11), benzoic acids (B12), quinolinecarboxylic acids (B13), nitriles (B14), benzamides (B15) and amides (B16).

9 Claims, No Drawings

HERBICIDAL MIXTURES CONTAINING PICOLINAFEN

CROSS REFERENCE TO RELATED APPLICATION

This application is a 35 USC §371 National Phase Entry Application from PCT/EP2004/002633, filed Mar. 12, 2004, and designating the United States, which claims the benefit of U.S. Provisional 60/453,975, filed Mar. 13, 2003.

The present invention relates to a herbicidal mixture comprising

A) picolinafen (I)

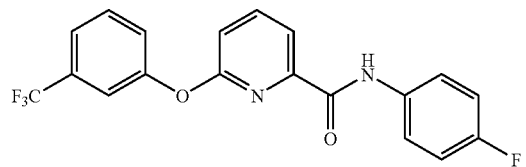

or the agriculturally useful salts thereof;

and

B) at least one further herbicide selected from the group of the phthalamates (B1), semicarbazones (B2), chloroacetanilides (B3), carbamates (B4), pyridazines (B5), dinitrophenols (B6), dipyridylenes (B7), benzothiadiazoles (B8), uracils (B9), pyridazinones (B10), phenylcarbamates (B11), benzoic acids (B12), quinolinecarboxylic acids (B13), nitriles (B14), benzamides (B15) and amides (B16);

and if desired

C) a safener selected from the group consisting of isoxadifen, mefenpyr and cloquintocet.

Moreover, the invention relates to herbicidal compositions comprising a mixture of components A and B and, if desired, component C and at least one liquid and/or solid carrier and, if desired, at least one surfactant.

Moreover, the invention relates to processes for preparing these mixtures or compositions and to methods for controlling unwanted vegetation.

Mixtures of picolinamides with other specific herbicides are known from WO 94/07368 and WO 01/26466. For crop protection compositions, it is desirable in principle to increase the specific activity of an active compound and to enhance the safety of action. It was an object of the present invention to increase the activity of picolinafen.

We have found that this object is achieved by the mixtures defined at the outset. Moreover, we have found herbicidal compositions comprising these mixtures and processes for their preparation and methods for controlling unwanted vegetation. In the last-mentioned methods it is immaterial whether components A, B and, if desired, C are formulated and applied jointly or separately, and, in the case of separate application, in which order the application is carried out.

The mixtures according to the invention show a synergistic effect; the compatibility of the herbicidally active components A) and B) with certain crop plants is generally maintained. However, it may be desirable to employ a component C) in an amount where a safening effect is observed.

Examples of herbicides which can be used in combination with picolinafen (A) and, if desired, component C) in accordance with the present invention are, inter alia:

B1: phthalamates, for example:
 naptalam;
B2: semicarbazones, for example:
 diflufenzopyr;
B3: chloroacetanilides, for example:
 dimethenamid, S-dimethenamid, acetochlor, alachlor, butachlor, butenachlor,
 diethatyl-ethyl, dimethachlor, metazachlor, metolachlor, S-metolachlor,
 pretilachlor, propachlor, prynachlor, terbuchlor, thenylchlor or xylachlor;
B4: carbamates, for example:
 asulam, carbetamid, chlorpropham, orbencarb, pronamid, propham or tiocarbazil;
B5: pyridazines, for example:
 dithiopyr or thiazopyr;
B6: dinitrophenols, for example:
 bromofenoxim, dinoseb, dinoseb-acetate, dinoterb, or DNOC;
B7: dipyridylenes, for example:
 cyperquat, difenzoquat, diquat or paraquat;
B8: benzothiadiazoles, for example:
 bentazone;
B9: uracils, for example:
 bromacil, isocil, lenacil or terbacil;
B10: pyridazinones, for example:
 chloridazon;
B11: phenylcarbamates, for example:
 desmedipham or phenmedipham;
B12: benzoic acids, for example:
 chloramben or dicamba;
B13: quinolinecarboxylic acids, for example:
 quinchlorac or quinmerac;
B14: nitriles, for example:
 dichlorbenil or chlorthiamid;
B15: benzamides, for example:
 isoxaben;
B16: amides, for example:
 allidochlor, benzoyl-ethyl, bromobutide, diphenamid, etobenzanid (benzochlomet), fosamine or monalide;

and the agriculturally useful salts thereof, or, if the compound is a carboxylic acid, the agriculturally useful esters, thioesters or amides thereof.

Picolinafen is known from EP 447 004.

The herbicides of component B) are known from

"Herbizide" [Herbicides], B. Hock, C. Fedtke, R. R. Schmidt, 1$^{st}$ edition, Thieme 1995 (quinchlorac (p. 238), butachlor (p. 32), pretilachlor (p. 32), di-thiopyr (p. 32), bromobutide (p. 243), bentazone (p. 30), chlorpropham (p. 205);

"Agricultural Chemicals", Book II Herbicides, 1993 (etobenzamid (HW-52)(p. 54), dimethenamid (p. 48), quinmerac (p. 233), metazachlor (p. 64), bromofenoxim (p. 228), thiazopyr (p. 226));

"Agricultural Chemicals", Book II Herbicides, 13$^{th}$ Edition (diflufenzopyr (p. 90), butenachlor (p. 54) tiocarbazil (p. 84));

Farm Chemicals Handbook 1994, Meister Publishing Company 1994 (isocil (p. C.200));

"Short Review of Herbicides & PGRs" 1991, Hodogaya Chemicals (thenylchlor (NSK-850) (p. 52), allidochlor (p. 48), benzoylprop-ethyl (p. 38), chlorthiamid (p. 150), diphenamid (p. 34), fosamine (p. 232), isoxaben (p. 42), monalide (p. 32), napthalam (p. 36), pronamid (p. 34), chloramben (p. 28), dicamba (p. 26), asulam (p. 112), carbetamid (p. 36), desmedipham (p. 104), orbencarb (p. 112), phenmedipham (p. 104), propham (p. 100), acetochlor (p. 48), alachlor (p. 46), diethathyl-ethyl (p. 48), demethachlor (p. 50), metolachlor (p. 46), propachlor (p. 44), prynachlor (p. 44), terbuchlor (p. 48), xylachlor (p. 52), dinoseb (p. 128), dinoseb-acetate (p. 128), dinoterb (p. 128), DNbC (p. 126), cyperquat-chloride (p. 158), difenzoquat (p. 160), diquat (p. 158), paraquat (p. 158), chloridazon (p. 174), bromacil (p. 180), lenacil (p. 180), terbacil (p. 180), dichlorbenil (p. 148), terbuchlor (p. 48)).

The safeners of component C) are known from

B. Hock, C. Fedtke, R. R. Schmidt, $1^{st}$ edition, Thieme 1995 (cloquinocet (p. 266));

Agrow 293 (11.28.97) (mefenpyr);

Agrow 324 (03.12.99) (isoxadifen).

The active compounds of the present invention can be present and used both in the form of the pure enantiomers and as racemates or diastereomer mixtures.

Furthermore, the active compounds can be used in the form of their agriculturally useful salts and, if the compounds are carboxylic acids, also in the form of their agriculturally useful esters, thioesters and amides.

Suitable salts are, in general, the salts of those cations, the acid addition salts of those acids or the esters, thioesters and amides whose cations or anions or esters, thioesters and amides have no adverse effect on the herbicidal action or the safening action.

Suitable cations are in particular alkali metal cations, such as lithium, sodium or potassium, or alkaline earth metal cations, such as magnesium or calcium. Also suitable are organic cations, such as phosphonium ions, sulfonium ions, preferably tri-($C_1$-$C_4$-alkyl)sulfonium, such as trimethylsulfonium, sulfoxonium ions, preferably tri-($C_1$-$C_4$-alkyl)sulfoxonium. Likewise suitable is ammonium, where, if desired, one to four hydrogen atoms can be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, dimethylammonium, trimethylammonium, tetramethylammonium, tetraethylammonium, isopropylammonium, diisopropylammonium, tetrabutyl-ammonium, ethanolammonium, diethanolammonium, 2-(2-hydroxyethoxy)ethyl-ammonium, benzyltrimethylammonium or benzyltriethylammonium.

Anions of useful acid addition salts are primarily halides, such as fluorides, chlorides, bromides or iodides, nitrates, hydrogensulfates, sulfates, dihydrogenphosphates, hydrogenphosphates, phosphates, methylsulfates, bicarbonates and carbonates.

Suitable esters are, for example, straight-chain or branched $C_1$-$C_{10}$-alkyl esters, in particular methyl, ethyl, propyl, isopropyl, butyl, isobutyl or isooctyl esters, or straight-chain or branched $C_1$-$C_4$-alkoxy-$C_1$-$C_4$-alkyl esters, in particular methoxyethyl, ethoxyethyl or butoxyethyl esters. Examples of thioesters are straight-chain or branched $C_1$-$C_{10}$-alkylthio esters, in particular ethylthio esters. Suitable for use as amides are, inter alia, methyl- or dimethylamides, and also anilides, such as anilide itself or 2-chloroanilide.

In a preferred embodiment, the herbicidal mixture according to the invention comprises A) picolinafen or an agriculturally useful salt thereof;

and

B) at least one further herbicide selected from the group of
B1: phthalamates, for example:
naptalam;
B2: semicarbazones, for example:
diflufenzopyr;
B3: chloroacetanilides, for example:
dimethenamid, S-dimethenamid, acetochlor, alachlor, butachlor,
butenachlor, diethatyl-ethyl, dimethachlor, metazachlor, metolachlor,
S-metolachlor, pretilachlor, propachlor, prynachlor, terbuchlor, thenylchlor or xylachlor;
B4: carbamates, for example:
asulam, carbetamid, chlorpropham, orbencarb, pronamid, propham or tiocarbazil;
B5: pyridazines, for example:
dithiopyr or thiazopyr;
B6: dinitrophenols, for example:
bromofenoxim, dinoseb, dinoseb-acetate, dinoterb or DNOC;
B7: dipyridylenes, for example:
cyperquat, difenzoquat, diquat or paraquat;
B8: benzothiadiazoles, for example:
bentazone;
B9: uracils, for example:
bromacil, isocil, lenacil or terbacil;
B10: pyridazinones, for example:
chloridazon;
B11: phenylcarbamates, for example:
desmedipham or phenmedipham;
B12: benzoic acids, for example:
chloramben or dicamba;
B13: quinolinecarboxylic acids, for example:
quinchlorac or quinmerac;
B14: nitriles, for example:
dichlorbenil or chlorthiamid;
B15: benzamides, for example:
isoxaben;
B16: amides, for example:
allidochlor, benzoyl-ethyl, bromobutide, diphenamid, etobenzanid (benzochlomet), fosamine or monalide;
and an agriculturally useful salt thereof, or, if the compound is a carboxylic acid, an agriculturally useful ester, thioester or amide thereof.

In a particularly preferred embodiment, the herbicidal mixture according to the invention comprises A) picolinafen or an agriculturally useful salt thereof and B) at least one further herbicide selected from the group consisting of
B7: dipyridylenes, for example
cyperquat, difenzoquat, diquat or paraquat;
B8: benzothiadiazoles, for example
bentazone;
B9: uracils, for example
bromacil, isocil, lenacil or terbacil;
B12: benzoic acids, for example
chloramben or dicamba;
B13: quinolinecarboxylic acids, for example
quinchlorac or quinmerac, in particular quinchlorac;
B15: benzamides, for example
isoxaben;

and an agriculturally useful salt thereof, or, if the compound is a carboxylic acid, an agriculturally useful ester, thioester or amide thereof.

In an especially preferred embodiment, the herbicidal mixture according to the invention comprises A) picolinafen or an agriculturally useful salt thereof and B) at least one further herbicide selected from the group consisting of
B7: dipyridylenes, for example
cyperquat, difenzoquat, diquat or paraquat;
B8: benzothiadiazoles, for example
bentazone;
B12: benzoic acids, for example
chloramben or dicamba;
B15: benzamides, for example
isoxaben;
and an agriculturally useful salt thereof, or, if the compound is a carboxylic acid, an agriculturally useful ester, thioester or amide thereof.

Extraordinary preference is given to herbicidal mixtures comprising picolinafen+difenzoquat, picolinafen+paraquat, picolinafen+bentazone, picolinafen+isocil, picolinafen+dicamba, picolinafen+quinchlorac, picolinafen+quinmerac or picolinafen+isoxaben.

In a most extraordinary embodiment, the herbicidal mixture comprises picolinafen+difenzoquat, picolinafen+bentazone, picolinafen+dicamba or picolinafen+isoxaben.

If the mixture comprises the active compounds paraquat or difenzoquat, preference is also given to those mixtures in which the active compounds mentioned above are present as chloride, bromide or methylsulfate salts.

If the mixture comprises the active compounds bentazone, dicamba or quinchlorac, preference is also given to those mixtures in which the active compounds mentioned above are present as trimethylsulfonium, ammonium, sodium, potassium, magnesium or calcium salts.

If the mixture comprises the active compounds dicamba or quinchlorac, preference is also given to those mixtures in which the active compounds mentioned above are replaced by their ethanolammonium, diethanolammonium, methylammonium, dimethylammonium, trimethylammonium, isopropylammonium or 2-(2-hydroxyethoxy)-ethylammonium salts, their methyl- or dimethylamides, their anilides or 2-chloro-anilides, their methyl, ethyl, propyl, isopropyl, butyl, isobutyl, isooctyl, methoxyethyl, ethoxyethyl, butoxyethyl esters or their ethyl thioesters.

In a further preferred embodiment, the herbicidal mixture according to the invention comprises A) picolinafen or an agriculaturally useful salt thereof;

and

B) at least one further herbicide selected from the group consisting of
B8: benzothiadiazoles, for example
bentazone;
B12: benzoic acids, for example
chloramben or dicamba;
B13: quinolinecarboxylic acids, for example
quinchlorac or quinmerac;
B15: benzamides, for example
isoxaben;
and an agriculturally useful salt thereof, or, if the compound is a carboxylic acid, an agriculturally useful ester, thioester or amide thereof.

Extraordinary preference is given to herbicidal mixtures comprising picolinafen+quinchlorac, picolinafen+quinmerac or pincolinofen+isoxaben.

If the mixture comprises the active compounds bentazone, dicamba, quinchlorac or quinmerac, preference is also given to those mixtures in which the active compounds above are present as trimethylsulfonium, ammonium, sodium, potassium, magnesium or calcium salts.

If the mixture comprises the active compounds dicamba, quinchlorac or quinmerac, preference is also given to those mixtures in which the active compounds mentioned are replaced by their ethanolammonium, dimethanolammonium, methylammonium, dimethylammonium, trimethylammonium, isopropylammonium or 2-(2-hydroxyethoxy)-ethylammonium salts, without methyl- or dimethylamides, their anilides or 2-chloro-anilides, and also methyl, ethyl, propyl, isopropyl, butyl, isobutyl, isooctyl, methoxy-ethyl, ethoxyethyl, butoxyethyl esters or their ethyl thioesters.

In a further particularly preferred embodiment, the herbicidal mixture according to the invention comprises A) picolinafen or an agriculturally useful salt thereof and B) at least one further herbicide, selected from the group consisting of
B2: semicarbazones, for example:
diflufenzopyr;
B3: chloroacetanilides, for example:
acetochlor, diethatyl-ethyl, dimethachlor, prynachlor, terbuchlor, thenylchlor or xylachlor;
B4: carbamates, for example:
carbetamid, chlorpropham, pronamid or propham;
B6: dinitrophenols, for example:
bromofenoxim, dinoseb, dinoseb-acetate or DNOC;
B7: dipyridylenes, for example:
cyperquat, difenzoquat, diquat or paraquat;
B9: uracils, for example:
isocil or lenacil;
B10: pyridazinones, for example:
chloridazon;
B11: phenylcarbamates, for example:
desmedipham or phenmedipham;
B13: quinolinecarboxylic acids, for example:
quinchlorac or quinmerac;
B15: benzamides, for example:
isoxaben;
B16: amides, for example:
allidochlor, benzoyl-ethyl, diphenamid, etobenzanid (benzochlomet), fosamine or monalide;
and an agriculturally useful salt thereof, or, if the compound is a carboxylic acid, an agriculturally useful ester, thioester or amide thereof.

In a particularly extraordinary embodiment, the herbicidal mixture according to the invention comprises picolinafen+difenzoquat or picolinafen+isoxaben.

In a further particularly preferred embodiment, the herbicidal mixture according to the invention comprises A) picolinafen or an agriculturally useful salt thereof and B) at least one further herbicide, selected from the group consisting of
B1: phthalamates, for example:
naptalam;
B2: semicarbazones, for example:
diflufenzopyr;

B3: chloroacetanilides, for example:
: dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;

B4: carbamates, for example:
: asulam, carbetamid, chlorpropham, orbencarb, pronamid, propham or tiocarbazil;

B5: pyridazines, for example:
: dithiopyr or thiazopyr;

B6: dinitrophenols, for example:
: bromofenoxim, dinoseb, dinoseb-acetate, dinoterb or DNOC;

B7: dipyridylenes, for example:
: cyperquat, difenzoquat, diquat or paraquat;

B8: benzothiadiazoles, for example:
: bentazone;

B9: uracils, for example:
: bromacil, isocil, lenacil or terbacil;

B10: pyridazinones, for example:
: chloridazon;

B11: phenylcarbamates, for example:
: desmedipham or phenmedipham;

B12: benzoic acids, for example:
: chloramben or dicamba;

B13: quinolinecarboxylic acids, for example:
: quinchlorac or quinmerac;

B14: nitriles, for example:
: dichlorbenil or chlorthiamid;

B15: benzamides, for example:
: isoxaben;

B16: amides, for example:
: allidochlor, benzoyl-ethyl, bromobutide, diphenamid, etobenzanid (benzochlomet), fosamine or monalide;

and an agriculturally useful salt thereof, or, if the compound is a carboxylic acid, an agriculturally useful ester, thioester or amide thereof;

and

C) a safener selected from the group consisting of isoxadifen, preferably isoxadifen "acid" or isoxadifen-ethyl, in particular isoxadifen-ethyl; mefenpyr, preferably mefenpyr "acid" or mefenpyr-diethyl, in particular mefenpyr-diethyl; and cloquintocet, preferably doquintocet "acid", cloquintocet-mexyl or cloquintocet-mexyl×n hydrate (n=2 to 6), in particular cloquintocet-mexyl.

In a further particularly preferred embodiment, the herbicidal mixture according to the invention comprises A) picolinafen or an agriculturally useful salt thereof, and B) at least one further herbicide, selected from the group consisting of B1: phthalamates, for example
: naptalam;

B2: semicarbazones, for example
: diflufenzopyr;

B3: chloroacetanilides, for example
: dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;

B4: carbamates, for example
: asulam, carbetamid, chlorpropham, orbencarb, pronamid, propham or tiocarbazil;

B5: pyridazines, for example
: dithiopyr or thiazopyr;

B6: dinitrophenols, for example
: bromofenoxim, dinoseb, dinoseb-acetate, dinoterb, or DNOC;

B10: pyridazinones, for example
: chloridazon;

B11: phenylcarbamates, for example
: desmedipham or phenmedipham;

B14: nitriles, for example
: dichlorbenil or chlorthiamid;

B15: benzamides, for example
: isoxaben;

B16: amides, for example
: allidochlor, benzoyl-ethyl, bromobutide, diphenamid, etobenzanid (benzochlomet), fosamine or monalide;

and an agriculturally useful salt thereof;

and

C) a safener selected from the group consisting of isoxadifen, preferably isoxadifen "acid" or isoxadifen-ethyl, in particular isoxadifen-ethyl, mefenpyr, preferably mefenpyr "acid" or mefenpyr-diethyl, in particular mefenpyr-diethyl, and cloquintocet, preferably cloquintocet "acid", cloquintocet-mexyl or cloquintocet-mexyl×n hydrate (n=2 to 6), in particular cloquintocet-mexyl.

In a further preferred embodiment, the herbicidal mixture comprises

A) picolinafen or an agriculturally useful salt thereof;

and

B) at least one further herbicide selected from the group consisting of

B7: dipyridylenes, for example
: cyperquat, difenzoquat, diquat or paraquat;

B8: benzothiadiazoles, for example
: bentazone;

B9: uraciles, for example
: bromacil, lenacil, terbacil or isocil;

B12: benzoic acids, for example
: chloramben or dicamba;

B13: quinolinecarboxylic acids, for example
: quinchlorac or quinmerac;

and an agriculturally useful salt thereof, or, if the compound is a carboxylic acid, an agriculturally useful ester, thioester or amide thereof;

and

C) a safener selected from the group consisting of isoxadifen, preferably isoxadifen "acid" or isoxadifen-ethyl, in particular isoxadifen-ethyl, mefenpyr, preferably mefenpyr "acid" or mefenpyr-diethyl, in particular mefenpyr-diethyl, and cloquintocet, preferably cloquintocet "acid", cloquintocet-mexyl or cloquintocet-mexyl×n hydrate (n=2 to 6), in particular cloquintocet-mexyl.

In a particularly preferred embodiment, the herbicidal mixture comprises

A) picolinafen or an agriculturally useful salt thereof;

and

B) at least one further herbicide selected from the group consisting of difenzoquat, paraquat, bentazone, isocil, dicamba and quinchlorac; or an agricultural salt thereof, or, if the herbicide is a carboxylic acid, an agriculturally useful ester, thioester or amide thereof;

and

C) isoxadifen-ethyl.

In a further particularly preferred embodiment, the herbicidal mixture comprises A) picolinafen or an agriculturally useful salt thereof, and B) at least one further herbicide selected from the group consisting of difenzoquat, paraquat, bentazone, isocil, dicamba and quinchlorac; or an agricultural salt thereof, or, if the herbicide is a carboxylic acid, an agriculturally useful ester, thioester or amide thereof;

and

C) mefenpyr-diethyl.

In a further particularly preferred embodiment, the herbicidal mixture comprises A) picolinafen or an agriculturally useful salt thereof;

and

B) at least one further herbicide selected from the group consisting of difenzoquat, paraquat, bentazone, isocil, dicamba and quinchlorac; or an agricultural salt thereof, or, if the herbicide is a carboxylic acid, an agriculturally useful ester, thioester or amide thereof;

and

C) cloquintocet, preferably cloquintocet "acid", cloquintocet-mexyl or cloquintocet-mexyl×n hydrate (n=2 to 6), in particular cloquintocet-mexyl.

In a further preferred embodiment, the herbicidal mixture comprises, in addition to picolinafen, only one further herbicide selected from the group B).

The corresponding preferences apply analogously to what was said above.

In a further preferred embodiment, the herbicidal mixture comprises, in addition to picolinafen, only one further herbicide selected from group B) and only one safener selected form group C).

The corresponding preferences apply analogously to what was said above.

Components A and B are applied in a synergistically effective amount; the mixing ratios of components A) to B) are usually within a weight ratio of from 1:0.1 to 1:50, preferably from 1:0.2 to 1:20.

If a safener C) is used, too, the mixing ratios of components A) to B) to C) are within a weight ratio of from 1:0.1:0.1 to 1:50:10, preferably from 1:0.2:0.2 to 1:20:4.

The present invention is also directed to herbicidal compositions comprising a herbicidally effective amount of a herbicidal mixture (comprising components A) and B) and, if desired, C), as described above), at least one liquid and/or solid carrier and, if desired, at least one surfactant.

The herbicidal mixtures and herbicidal compositions according to the invention allow very good control of broad-leaf weeds and weed grasses in crops such as corn, cereals, rice and soybeans, in particular in cereals, without damaging the crop plant; an effect which occurs in particular also at low application rates.

Taking into account the universality of the application methods, the synergistic herbicidal mixtures and herbicidal compositions according to the invention can additionally be employed in a further number of crop plants for eliminating undesirable plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the herbicidal mixtures and herbicidal compositions according to the invention can also be used in crops which tolerate the action of herbicides owing to breeding, including genetic engineering methods. Suitable are preferably genetically engineered cereals which are resistant against glyphosate or against herbicidal ALS inhibitors, such as, for example, sulfonylureas or imidazolinones.

The mixtures according to the invention or the herbicidal compositions comprising them can be used, for example, in the form of directly sprayable aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or watering.

The use forms depend on the intended purposes; in each case, they should ensure the finest possible distribution of the active compounds according to the invention.

The herbicidal compositions comprise components A) and B) and, if desired, C) and auxiliaries customary for formulating crop protection agents.

Suitable inert additives are mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydro-naphthalene, alkylated naphthalenes or derivatives thereof, alkylated benzenes or derivatives thereof, alcohols, such as methanol, ethanol, propanol, butanol, cyclohexanol, ketones, such as cyclohexanone, strongly polar solvents, such as N-methyl-pyrrolidone or water.

Aqueous use forms can be prepared from emulsion concentrates, suspensions, pastes, wettable powders or water-dispersible granules by adding water. To prepare emulsions, pastes or oil dispersions, components A), B) and, if desired, C), as such or dissolved in an oil or solvent, can be homogenized in water using a wetting agent, tackifier, dispersant or emulsifier. Alternatively, it is possible to prepare concentrates comprising active compound, wetting agent, tackifier, dispersant or emulsifier and, if appropriate, solvent or oil, which are suitable for dilution with water.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the synergistic herbicidal mixture or the individual active compounds with a solid carrier.

Granules, for example coated granules, impregnated granules and homogeneous granules can be prepared by binding the active compounds to solid carriers. Solid carriers are mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, treebark meal, wood meal and nutshell meal, cellulose powders, or other solid carriers.

The concentrations of the mixtures according to the invention in the ready-to-use preparations can be varied within wide ranges. In general, the formulations comprise from about 0.001 to 98% by weight, preferably from 0.01 to 95% by weight, in particular from 0.5 to 90% by weight, of active compounds.

The active compounds of components A) and B) and, if desired, C) can be formulated jointly, but also separately, and/or applied jointly or separately to the plants, their habitat and/or seeds. The active compounds are preferably applied simultaneously. However, it is also possible to apply them separately.

Moreover, it may be useful to apply the herbicidal mixtures or herbicidal compositions according to the invention jointly or separately with further crop protection agents, for example with agents for controlling pests or phytopathogenic fungi or bacteria. Of interest is furthermore the miscibility with mineral salt solutions employed for treating nutritional and trace element deficiencies. Non-phytotoxic oils and oil concentrates may also be added.

The mixtures and herbicidal compositions according to the invention can be applied by the pre-emergence or by the post-emergence method. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of the undesirable plants growing underneath, or the bare soil surface (post-directed, lay-by).

In the case of post-emergence treatment, the herbicidal compositions according to the invention are applied to the plants mainly by spraying the leaves. Here, the application can be carried out by customary spraying techniques using, for example, water as carrier and amounts of spray liquor of from about 100 to 1000 I/ha. Application of the compositions by the low-volume and ultra-low-volume method and their application in the form of granules is also possible.

The required application rate of pure active compound mixture, i.e. A) and B) and, if desired, C), without formulation auxiliary, is, depending on the composition of the plant stand, and depending on the developmental stages of the plants, the climatic conditions and the application technique, in general from 0.001 to 3.0 kg/ha, preferably from 0.01 to 2.5 kg/ha, in particular from 0.01 to 1.0 kg/ha, of active substance (a.s.)

The application rate of picolinafen is generally from 0.01 to 0.5 kg/ha of active substance (a.s.).

The application rate of component B) is generally from 0.01 to 2.0 kg/ha of active substance (a.s.).

The application rate of component C) is generally from 0.01 to 0.5 kg/ha of active substance (a.s.).

USE EXAMPLES

The mixtures according to the invention were applied by the pre-emergence method or by the post-emergence method (foliar treatment).

Some of the experiments were greenhouse experiments, while others were carried out in the open in small plots (on a site with sandy loam soil (pH 6.2 to 7.0) or sandy clay soil (pH 5.0 to 6.7)).

The harmful plants came in different sizes and developmental stages, averaging 5 to 20 cm, depending on their habit.

The herbicidally active compounds of components A) and B) and, if desired, the safeners C) were applied in succession or jointly, in the latter case as a tank mix in some cases and as a readymix in other cases, in the form of emulsions, aqueous solutions or suspensions, the vehicle used being water (300-400 I/ha). In the experiments in the open, application was effected with the aid of a mobile plot sprayer.

The experimental period extended over 3 to 8 weeks; observations on the stand were also made at later points in time.

The damage caused by the herbicidal compositions was assessed using a scale from 0% to 100% in comparison with untreated control plots. 0 means no damage and 100 means complete destruction of the plants.

The examples below demonstrate the effect of the herbicidal compositions which can be used in accordance with the invention, without excluding the possibility of other applications.

In these examples, the method of S. R. Colby (Calculating synergistic and antagonistic responses of herbicide combinations, Weeds 15, 20 ff (1967)) was used to calculate the value E which can be expected if the action of the individual active compounds is merely additive.

The calculation was based on the formula $$E = X + Y - \frac{XY}{100}$$

where

X=percentage of the herbicidal action of component A) at an application rate of a;

Y=percentage of the herbicidal action of component B) at an application rate of b;

E=herbicidal action of components A)+B) to be expected at application rates a+b (in %).

If the observed value exceeds the value E calculated using Colby's formula, synergism is present.

The herbicidal mixtures according to the invention, such as, for example, picolinafen+difenzoquat, picolinafen+bentazone, picolinafen+dicamba or picolinafen+isoxaben, applied at appropriate application rates by the post-emergence method, have a more potent herbicidal action than would be expected in accordance with Colby based on the observed effects of the individual components when used alone.

We claim:

1. A herbicide, consisting essentially of a synergistic mixture of:
   A) picolinafen (I)

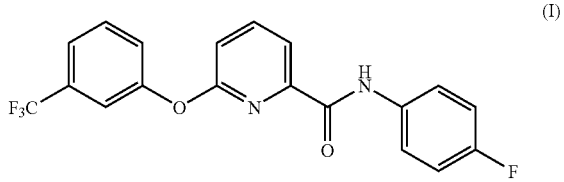

or an agriculturally useful salt thereof,
   and
   B) at least one further herbicide selected from the group consisting of dicamba and quinmerac, the agriculturally useful salts thereof and the agriculturally useful esters, thioesters and amides thereof, and
   wherein component A) and component B) are present in a weight ratio of from 1:8 to 2:1 for picolinafen:dicamba or from 1:5 to 1:1.25 for picolinafen:quinmerac.

2. A herbicide as claimed in claim 1, wherein component B) is dicamba or quinmerac.

3. A herbicidal composition consisting essentially of a herbicidally effective amount of a mixture as claimed in claim 1, at least one inert liquid and/or solid carrier and, if desired, at least one surfactant to prepare said composition.

4. A process for preparing herbicidal compositions as claimed in claim 3, which comprises mixing component A), component B), at least one inert liquid and/or solid carrier and, if desired, a surfactant.

5. A method for controlling unwanted vegetation, which comprises simultaneously or successively applying to unwanted plants, their habitat and or seeds a herbicide as claimed in claim 1 before, during and/or after emergence of the unwanted plants, where components A), B) and, if desired, C), a safener selected from the group consisting of isoxadifen, mefenpyr and cloquintocet, can be applied jointly or separately.

6. A method for controlling unwanted vegetation as claimed in claim 5, wherein the herbicide is applied to leaves of crop plants and of the unwanted plants.

7. A method for controlling undesired vegetation comprising simultaneously or successively applying to undesired plants, their habitat or their seeds a synergistic mixture consisting essentially of:
   A) picolinafen (I)

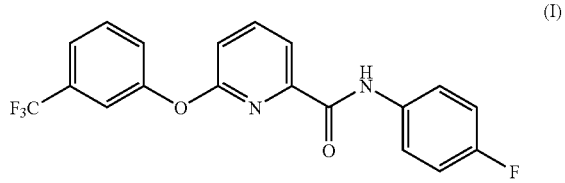

or an agriculturally useful salt thereof,
   and
   B) at least one further herbicide selected from the group consisting of dicamba and quinmerac, the agriculturally useful salts thereof and the agriculturally useful esters, thioesters and amides thereof, and
   wherein component A) and component B) are present in a weight ratio of from 1:8 to 2:1 for picolinafen:dicamba or from 1:5 to 1:1.25 for picolinafen:quinmerac.

8. The herbicide of claim 1, further consisting of component C), a safener selected from the group consisting of isoxadifen, mefenpyr and cloquintocet.

9. The process as claimed in claim 4, wherein the process further includes mixing a safener selected from the group consisting of isoxadifen, mefenpyr, and cloquintocet with the other components.

* * * * *